United States Patent
Attolino

(10) Patent No.: US 9,783,485 B1
(45) Date of Patent: Oct. 10, 2017

(54) CRYSTALLINE INHIBITOR OF 4-HYDROXYPHENYLPYRUVATE DIOXYGENASE, AND A PROCESS OF SYNTHESIS AND CRYSTALLIZATION THEREOF

(71) Applicant: Dipharma S.A., Chiasso (CH)

(72) Inventor: Emanuele Attolino, Baranzate (IT)

(73) Assignee: Dipharma S.A., Chiasso (CH)

( * ) Notice: Subject to any disclaimer, the term of this patent is extended or adjusted under 35 U.S.C. 154(b) by 0 days.

(21) Appl. No.: 15/364,576

(22) Filed: Nov. 30, 2016

(51) Int. Cl.
   *C07C 205/46* (2006.01)

(52) U.S. Cl.
   CPC ........ *C07C 205/46* (2013.01); *C07B 2200/13* (2013.01)

(58) Field of Classification Search
   CPC .......................... C07C 205/46; C07B 2200/13
   See application file for complete search history.

(56) References Cited

U.S. PATENT DOCUMENTS

| | | |
|---|---|---|
| 4,695,673 A | 9/1987 | Heather et al. |
| 5,006,158 A | 4/1991 | Carter et al. |
| 5,550,165 A | 8/1996 | Ellis et al. |
| 8,354,451 B2 | 1/2013 | Moran et al. |

FOREIGN PATENT DOCUMENTS

| | | |
|---|---|---|
| EP | 0 805 791 B1 | 2/1999 |
| EP | 0 591 275 B1 | 3/1999 |
| EP | 1 853 241 B1 | 9/2011 |
| WO | WO 2010/054273 A1 | 5/2010 |
| WO | WO 2011/106655 A1 | 9/2011 |

OTHER PUBLICATIONS

U.S. Dept. of Health and Human Services, Food and Drug Administration, CDER, CBER, "M7 Assessment and Control of DNA Reactive (Mutagenic) Impurities in Pharmaceuticals to Limit Potential Carcinogenic Risk, Guidance for Industry," ICH; 1-31 (May 2015).

Introne, W. J., et al., "A 3-year Randomized Therapeutic Trial of Nitisinone in Alkaptonuria," *Mol. Genet. Metab.*; 103(4): 307-314. doi:10.1016/j.ymgme.2011.04.016 (Aug. 2011).

*Primary Examiner* — Sudhakar Katakam

(74) *Attorney, Agent, or Firm* — Sterne, Kessler, Goldstein & Fox P.L.L.C.

(57) ABSTRACT

The present invention relates to an improved synthesis and crystallization process of the 4-hydroxyphenylpyruvate dioxygenase (HPPD) inhibitor 2-(2-nitro-4-trifluoromethylbenzoyl)-1,3-cyclohexanedione, also known as nitisinone or NTBC.

13 Claims, 1 Drawing Sheet

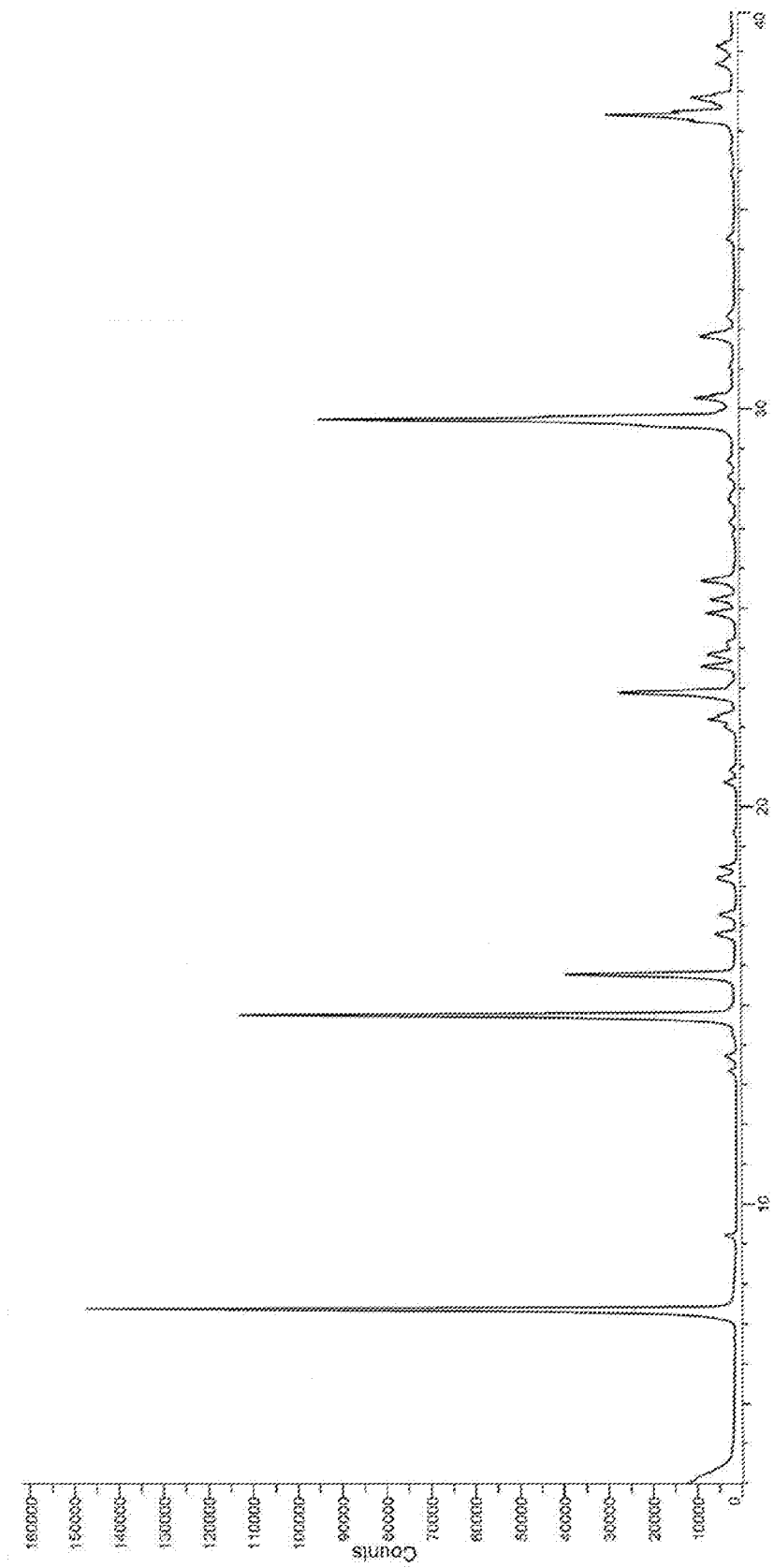

CRYSTALLINE INHIBITOR OF 4-HYDROXYPHENYLPYRUVATE DIOXYGENASE, AND A PROCESS OF SYNTHESIS AND CRYSTALLIZATION THEREOF

FIELD OF THE INVENTION

The present invention relates to an improved synthesis and crystallization process of 4-hydroxyphenylpyruvate dioxygenase (HPPD) inhibitor 2-(2-nitro-4-trifluoromethylbenzoyl)-1,3-cyclohexanedione, also known as nitisinone or NTBC. This new process of synthesis and crystallization gives rise to an extremely pure and stable 2-(2-nitro-4-trifluoromethylbenzoyl)-1,3-cyclohexanedione.

BACKGROUND OF THE INVENTION

NTBC is a drug marketed by Swedish Orphan Biovitrum International AB under the brand name Orfadin® and it is used to slow the effects of hereditary tyrosinemia type 1 (HT-1) in adult and pediatric patients. It has been approved by FDA and EMA in January 2002 and February 2005 respectively.

HT-1 disease is due to a deficiency of the final enzyme of the tyrosine catabolic pathway fumarylacetoacetate hydrolase. NTBC is a competitive inhibitor of 4-hydroxyphenylpyruvate dioxygenase (HPPD), an enzyme which precedes fumarylacetoacetate hydrolase. By inhibiting the normal catabolism of tyrosine in patients with HT-1, NTBC prevents the accumulation of the toxic intermediates maleylacetoacetate and fumarylacetoacetate, that in patients with HT-1 are converted to the toxic metabolites succinylacetone and succinylacetoacetate, the former inhibiting the porphyrin synthesis pathway leading to the accumulation of 5-aminolevulinate.

Usefulness of NTBC in the treatment of further diseases has also been documented. A non-comprehensive list is reported hereinafter.

Effectiveness of Orfadin® in the treatment of diseases where the products of the action of HPPD are involved (e.g., HT-1) has been described notably in EP0591275B1 corresponding to U.S. Pat. No. 5,550,165B1. Synthesis of NTBC is also described in this patent.

WO2011106655 reports a method for increasing tyrosine plasma concentrations in a subject suffering from oculocutaneous/ocular albinism, the method comprising administering to the subject a pharmaceutically acceptable composition comprising NTBC in the range of between about 0.1 mg/kg/day to about 10 mg/kg/day.

U.S. Pat. No. 8,354,451B2 reports new methods of combating microbial infections due to fungi or bacteria by means of administration to a subject of a therapeutically active amount of NTBC.

WO2010054273 discloses NTBC-containing compositions and methods for the treatment and/or prevention of restless leg syndrome (RLS).

EP1853241B1 claims the use of NTBC in the treatment of a neurodegenerative disease, notably Parkinson disease.

Introne W. J., et al., disclosed usefulness of nitisinone in the treatment of alkaptonuria (Introne W. J., et al., Molec. Genet. Metab., 2011, 103, 4, 307). The key step of the synthesis reported in EP0591275B1 (now propriety of Swedish Orphan Biovitrum International AB, SE), involves the reaction of 2-nitro-4-trifluromethylbenzoyl chloride and cyclohexane-1,3-dione in the presence of triethylamine and then use of acetone cyanohydrin in order to promote the rearrangement of the key intermediate enol ester. After washing and extraction from $CH_2Cl_2$, the crude product is recrystallized from ethyl acetate to get the desired 2-(2-nitro-4-trifluoromethylbenzoyl)-1,3-cyclohexanedione as a solid having a melting point of 88-94° C.

Another patent (U.S. Pat. No. 4,695,673) filed in name of Stauffer Chemical Company disclosed a process of synthesis of acylated 1,3-dicarbonyl compounds in which the intermediate enol ester is isolated prior to its rearrangement into the final product, said rearrangement making use of a cyanohydrin compound derived from alkali metal, methyl alkyl ketone, benzaldehyde, cyclohexanone, $C_2$-$C_5$ aliphatic aldehyde, lower alkyl silyl or directly by using hydrogen cyanide.

Yet another patent (U.S. Pat. No. 5,006,158) filed in name of ICI Americas Inc. disclosed a process similar to the one disclosed in U.S. Pat. No. 4,695,673 wherein the intermediate enol ester was isolated prior to its rearrangement into the final product by use of potassium cyanide. Said reaction can optionally be done by concomitant use of a phase transfer catalyst such as Crown ethers. The preferred solvent for conducting such a reaction is 1,2-dichloroethane.

Still a further patent (EP0805791) filed in name of Zeneca Ltd disclosed an alternative synthesis of nitisinone involving the reaction of 1,3-cyclohexanedione and variously substituted benzoyl chloride in the presence of sodium or potassium carbonate in $CH_3CN$ or DMF. Best yields were obtained using $CH_3CN$ as solvent and sodium carbonate as the base. Reaction was performed at 55-57° C. in 17 hours.

It is well known that one of the problems of the actual drug formulation (i.e., Orfadin® capsules) is its chemical instability. Indeed, even if Orfadin® has to be stored in a refrigerator at a temperature ranging from 2° C. to 8° C., its shelf life is of only 18 months. After first opening, the in-use stability is a single period of 2 months at a temperature not above 25° C., after which it must be discarded. It will be evident that such storage conditions have an impact in the distribution chain of the medicine, in terms of costs and also in terms of logistics for the patient. Therefore, there is an urgent need of more stable formulations, both from a logistic supply chain point of view, and from the patient compliance point of view. Since the formulation of Orfadin® contains only the active ingredient and starch as excipient, relative instability may be attributed to the active pharmaceutical ingredient itself; in other words it can derive from the way it is synthesized and/or the way it is extracted from the reaction mixture, and/or the way it is finally crystallized. Furthermore, some impurities may contribute to render the final product less stable overtime. Consequently, it is of major importance to identify a process of synthesis and/or a crystallization method that enable the reliable production of a highly pure and stable product.

Impurities as herein-above mentioned can derive either from the final product itself (through chemical degradation) or directly from the starting materials/solvents used in the process of synthesis. Regarding the latter option, it is therefore primordial to ascertain that at each step, impurities are completely removed in order not to get them at the final stage, also considering that some of them could potentially be cyto/genotoxic.

The impurities correlated to nitisinone can be either derived from the starting materials themselves (i.e., impurities 1 and 2) or obtained as side products during the process of synthesis and/or under storage conditions (i.e., impurities 3 to 5) and are the following:

2-nitro-4-(trifluoromethyl) benzoic acid (Impurity no 1),
1,3-cyclohexanedione (CHD) (Impurity no 2),
4-(trifluoromethyl)salicylic acid (Impurity no 3),
2-[3-nitro-4-(trifluoromethyl)benzoyl]-1,3-cyclohexanedione (Impurity no 4), and
6-trifluoromethyl-3,4-dihydro-2H-xanthene-1,9-dione (Impurity no 5).

Scheme 1

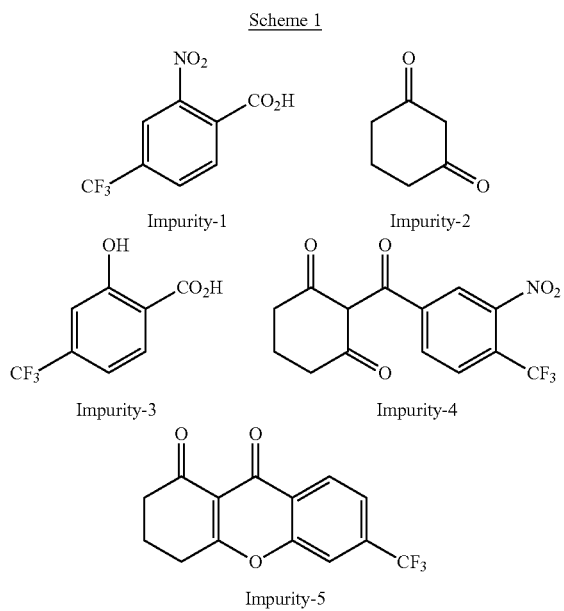

Impurity-2, impurity-3, and impurity-5 have been previously reported in WO2015101794. Strangely, impurity-4 has never been reported, even if it is an obvious side-product which can easily be formed during the coupling reaction between 1,3-cyclohexanedione and 2-nitro-4-(trifluoromethyl) benzoic acid, the latter being not 100% pure but containing some amount of regioisomer 3-nitro-4-(trifluoromethyl) benzoic acid.

Potential genotoxicity of impurity no 4 which possesses an aromatic nitro moiety was assessed using in-silico techniques and resulted to be a potential genotoxic impurity. According to the FDA ICH M7 guidelines, daily intake of a mutagenic impurity (Threshold of Toxicological Concern, TTC) in an amount not greater than 1.5 μg per person is considered to be associated with a negligible risk to develop cancer over a lifetime of exposure. Consequently, assuming a daily dose of 2 mg/kg, for a person weighing 70 kg, the maximum tolerated impurity content of such a compound would be of about 11 ppm, as calculated according to the equation underneath.

$$\text{concentration limit(ppm)} = \frac{TTC(\mu g/day)}{Dose(g/day)}$$

It is therefore of paramount importance to ensure that the process of synthesis of nitisinone and the purification steps of the same give rise to an API devoid of such impurity no 4, or at least far below the threshold of 11 ppm as indicated above. The skilled person will understand that total absence of said impurity is highly desirable.

It is well known in the pharmaceutical field that investigation of potential polymorphism of a solid API is of crucial importance and is also recommended by major regulatory authorities such as FDA.

Notwithstanding the fact that nitisinone has been used for years to treat HT-1 patients, it appears that no NTBC formulation fully satisfies the requisites of stability and/or compliance standard for the patients. Therefore, there is an unmet medical need of long-term pure and stable formulations.

DESCRIPTION OF THE INVENTION

It has been surprisingly found that nitisinone obtained through the process, object of a first embodiment of the instant invention is not only highly pure, but also extremely stable. This process of synthesis encompasses a crystallization step of 2-(2-nitro-4-trifluoromethylbenzoyl)-1,3-cyclohexanedione by means of toluene and traces amount of acetonitrile.

While not intending to be bound in any way by any theory, it is believed that the improved chemical stability of nitisinone is attributable to its crystalline purity obtainable through the presently claimed invention.

The expressions "extremely stable" and/or "long term stable" and/or "highly stable" shall be understood for purposes of the present invention to mean that the chemical integrity of nitisinone is of at least 95% after one month of storage of nitisinone at 25° C. and 60% RH.

When referring to purity determined by HPLC techniques, said chromatograms are gathered at a wavelength of 235 nm.

When referring to temperatures and/or pH, the term "about" shall be understood for purposes of the present invention to mean plus or minus 10% of the temperature and/or pH values mentioned, preferably plus or minus 5% and even more preferably plus or minus 1%.

In one embodiment, said chemical integrity is of at least 96% after six months of storage of nitisinone at 25° C. and 60% RH.

In another embodiment, said chemical integrity is of at least 97% after six months of storage of nitisinone at 25° C. and 60% RH.

In a preferred embodiment, said chemical integrity is of at least 98% after six months of storage of nitisinone at 25° C. and 60% RH.

In a still preferred embodiment, said chemical integrity is of at least 99% after six months of storage of nitisinone at 25° C. and 60% RH.

Another embodiment of the invention contemplates chemical integrity of nitisinone after nine months of storage at 25° C. and 60% RH.

In said embodiment, the chemical integrity of nitisinone is of at least 95% after nine months of storage of nitisinone at 25° C. and 60% RH.

In a preferred embodiment, the chemical integrity of nitisinone is of at least 96% after nine months of storage of nitisinone at 25° C. and 60% RH.

In another preferred embodiment, the chemical integrity of nitisinone is of at least 97% after nine months of storage of nitisinone at 25° C. and 60% RH.

In a still preferred embodiment, the chemical integrity of nitisinone is of at least 98% after nine months of storage of nitisinone at 25° C. and 60% RH.

In a still more preferred embodiment, the chemical integrity of nitisinone is of at least 99% after nine months of storage of nitisinone at 25° C. and 60% RH.

Another embodiment of the invention contemplates chemical integrity of nitisinone after six months of storage at 40° C. and 75% RH.

In said embodiment, the chemical integrity of nitisinone is of at least 95% after six months of storage of nitisinone at 40° C. and 75% RH.

In a preferred embodiment, the chemical integrity of nitisinone is of at least 96% after six months of storage of nitisinone at 40° C. and 75% RH.

In another preferred embodiment, the chemical integrity of nitisinone is of at least 97% after six months of storage of nitisinone at 40° C. and 75% RH.

In a still preferred embodiment, the chemical integrity of nitisinone is of at least 98% after six months of storage of nitisinone at 40° C. and 75% RH.

In a still more preferred embodiment, the chemical integrity of nitisinone is of at least 99% after six months of storage of nitisinone at 40° C. and 75% RH.

In an even more preferred embodiment, nitisinone is in crystalline form and contains less than 10 ppm of 2-[3-nitro-4-(trifluoromethyl)benzoyl]-1,3-cyclohexanedione and less than 0.05% of any single impurities chosen from the group consisting of 2-nitro-4-(trifluoromethyl) benzoic acid, 1,3-cyclohexanedione, 4-(trifluoromethyl)salicylic acid, and 6-trifluoromethyl-3,4-dihydro-2H-xanthene-1,9-dione, after storage for six months at a temperature of 40° C. and 75% relative humidity.

It is submitted that testing at 40° C. and 75% RH for a short time such as six months, is considered indicative of stability at 25° C. (i.e., room temperature) for a longer period of time (fifteen to eighteen months).

An embodiment of this invention consists of a process to synthesize nitisinone, by reacting 2-nitro-4-(trifluoromethyl) benzoyl chloride and 1,3-cyclohexanedione in acetonitrile solution in the presence of potassium carbonate.

In a more preferred embodiment, nitisinone is obtained highly pure by subsequent crystallization.

In a still more preferred embodiment, the crystallization is obtained by means of toluene.

In an even more preferred embodiment, the crystallization process encompasses the following steps:
  a) adding crude nitisinone to an approximately 3/1 binary acetonitrile/toluene mixture, wherein the ratio nitisinone/binary mixture is around ¼ (w/v) and heating at a temperature of about 55° C. until complete dissolution;
  b) concentrating the solution from step a) to a final volume roughly twice the initial volume of toluene added in step a) at a temperature below 50° C. in order to obtain a solution of nitisinone in toluene containing approximatively 0.5-0.6 g of nitisinone per ml of solvent;
  c) adding toluene to the mixture obtained in step b) in order to double the final volume obtained from step b);
  d) repeating step b);
  e) heating to about 55° C. for 1 h;
  f) cooling slowly to about 10° C. in 10 to 12 h;
  g) filtering off the solid thus obtained in step f) and rinsing it with pre-cooled toluene; and
  h) drying the crystals under vacuum at a temperature of about 60° C. for 4 h.

In another embodiment, the present invention provides nitisinone Form A, having an impurity 2-nitro-4-(trifluoromethyl) benzoic acid (Impurity no 1) in an amount less than about 0.10 area percent and more preferably less than 0.05%, as measured by HPLC/MS.

In yet another embodiment, the present invention provides nitisinone Form A, having an impurity 1,3-cyclohexanedione (CHD) (Impurity no 2) in an amount less than about 0.10 area percent and more preferably less than 0.05%, as measured by HPLC/MS.

In a still further embodiment, the present invention provides nitisinone Form A, having an impurity 4-(trifluoromethyl)salicylic acid (Impurity no 3) in an amount less than about 0.10 area percent and more preferably less than 0.05%, as measured by HPLC/MS.

In a yet still further embodiment, the present invention provides nitisinone Form A, having an impurity 2-[3-nitro-4-(trifluoromethyl)benzoyl]-1,3-cyclohexanedione (Impurity no 4) in an amount less than about 10 ppm and more preferably less than 5 ppm, as measured by HPLC/MS.

In another embodiment, the present invention provides nitisinone Form A, having an impurity 6-trifluoromethyl-3,4-dihydro-2H-xanthene-1,9-dione (Impurity no 5) in an amount less than about 0.10 area percent and more preferably less than 0.05%, as measured by HPLC/MS.

In another preferred embodiment, the present invention provides nitisinone Form A, having a total amount of impurities 1 to 5 less than about 0.50 area percent and more preferably less than 0.25%, as measured by HPLC/MS.

In a still even more preferred embodiment, the present invention contemplates nitisinone crystalline Form A having a purity of at least 99.94%.

In a still further even more preferred embodiment, the present invention contemplates nitisinone crystalline Form A having a purity of at least 99.94% and containing less than 10 ppm of impurity no 4, preferably less than 5 ppm, ideally less than 1 ppm.

In a further preferred embodiment, nitisinone crystals have a PSD (d90) between 310 to 350 μm.

Another embodiment of the present invention consists of a crystalline pure nitisinone Form A, which has a X-ray powder diffraction pattern with at least five specific peaks at about 2-theta=7.4, 14.7, 15.7, 22.9, and 29.7, wherein said values may be plus or minus 0.2° 2-theta and have an intensity of at least 30%. In a further embodiment of the present invention, the crystalline pure nitisinone Form A has a X-ray powder diffraction pattern with at least ten specific peaks at about 2-theta=7.4, 14.7, 15.7, 22.9, 23.5, 23.8, 25.7, 29.7, 30.3, and 31.9 wherein said values may be plus or minus 0.2° 2-theta.

Another aspect of the instant invention regards usefulness of the thus obtained crystalline Form A nitisinone active ingredient in a pharmaceutical formulation as a medicament due to its 4-hydroxyphenylpyruvate dioxygenase inhibiting properties for the treatment of disorders where such inhibition results in improving the health of the patient. In particular, patients suffering from HT-1, or from oculocutaneous/ocular albinism, or from microbial infections due to fungi or bacteria, or from restless leg syndrome, or from neurodegenerative disease, notably Parkinson disease can be treated.

In a preferred embodiment of the present invention, the pharmaceutical formulation is for treating patients suffering from HT-1.

In accordance with the foregoing, there are provided methods of inhibiting 4-hydroxyphenylpyruvate dioxygenase enzyme in a patient. The methods include administering an effective amount of the crystalline 2-(2-nitro-4-trifluoromethylbenzoyl)-1,3-cyclohexanedione described herein to a patient in need thereof. Within this aspect of the invention, patients requiring inhibition of the 4-hydroxyphenylpyruvate dioxygenase enzyme will be those suffering from diseases such as oculocutaneous/ocular albinism, microbial infections, restless leg syndrome, alkaptonuria, and hereditary tyrosinemia type 1. Preferred aspects of this embodiment include treating hereditary tyrosinemia type 1.

Generally, the pharmaceutical formulation of the present invention is administered in a "therapeutically effective amount". The amount of the pharmaceutical formulation actually administered will typically be determined by a physician, in the light of the relevant circumstances, including the condition to be treated, any other potential drug the patient is currently taking, the age, the sex, body weight, and response of the individual patient, the severity of the patient's symptoms, and the like. Generally, however, the crystalline Form A nitisinone is administered in amounts ranging from between about 0.1 mg/kg/day to about 2 mg/kg/day, with amounts of from about 1-2 mg/kg/day being preferred. A further embodiment of the present invention consists of a pharmaceutical formulation comprising nitisinone obtained by the process described in example 2. It is submitted that testing at 40° C. and 75% RH for a short time such as six months, is considered indicative of stability at 25° C. (i.e., room temperature) for a longer period of time (fifteen to eighteen months).

DESCRIPTION OF THE DRAWING

FIG. 1: represents the X-ray spectra of 2-(2-nitro-4-trifluoromethylbenzoyl)-1,3-cyclohexanedione Form A polymorph.

EXAMPLES

Abbreviations:
CH₃CN: acetonitrile
HCl: hydrochloric acid
HPLC: high-performance liquid chromatography
HPLC/MS: high-performance liquid chromatography-mass spectrometry
General Remarks:

Crystalline form has been characterised by Bruker D8 Advance X-ray powder diffraction (XRPD), Bragg-Brentano geometry, CuKα radiation with wavelength λ=1.54; scanning with 2θ angle range of 3° to 40°, step size of 0.02° for 0.5 seconds per step. Linear solid-state detector (Lynx Eye). Micronization has been performed with a laboratory scale micronizer FLUID JET MILL J-20 (Tecnologia Meccanica Srl) using the following milling conditions:

Grind air: dry nitrogen gas
Ring pressure: 3.9 bar
Venturi pressure: 4.1 bar
Feed rate: 0.30 g/min Particle size and d(90) has been determined using laser light scattering technique using a Malvern Mastersizer 3000 and water as dispersant.

Example 1

Thionyl chloride (162 g, 1.36 mol) was added dropwise into a suspension of 2-nitro-4-trifluoromethylbenzoic acid (228 g, 0.97 mol) in toluene (630 g) at 80° C. The thus obtained solution was kept under stirring at 80° C. for 20 hours, and then cooled to 50° C. The volatiles were removed under reduced pressure in order to get the expected 2-nitro-4-trifluoromethylbenzoyl chloride as an oil. The latter, cooled to 25° C. was added dropwise to a suspension of 1,3-cyclohexanedione (109 g, 0.97 mol) and potassium carbonate (323 g, 2.33 mol) in CH₃CN (607 g). After 18 h the mixture was diluted with water (500 ml) and slowly acidified to about pH=1 with HCl 37%. The mixture was then warmed to about 55° C. and the phases were separated. The organic layer was washed with a 10% aqueous solution of sodium chloride and then, concentrated under reduced pressure at a temperature below 55° C. to reach a volume of 380 ml. The thus obtained mixture was stirred at 55° C. for 1 h and then cooled to 0° C. in 16 to 18 h. The resulting solid was filtered and rinsed several times with pre-cooled (0° C.) toluene. The wet solid was dried at 60° C. under vacuum for 6 h to provide nitisinone (164 g) as a white to yellowish solid with a purity of 98.4% as measured by HPLC and a content of potentially genotoxic impurity no 4 of 6.1 ppm measured by HPLC/MS.

Example 2

Nitisinone as obtained from example 1 (164 g) was added to a 3/1 (w/w) mixture of CH₃CN/toluene (volume of solvent: 638 ml). The mixture was warmed gently to about 55° C. under stirring until solids were completely dissolved. The solution was then concentrated under reduced pressure maintaining the internal temperature below 50° C. to reach a volume of 290 ml. Then, more toluene (255 g) was added and the solution was concentrated again under reduced pressure until the residual volume reached 290 ml. The solution was heated to about 55° C. for 1 h and successively cooled slowly in 10 to 12 h to 10° C. The resulting solid was filtered and rinsed several times with pre-cooled (0° C.) toluene. The wet solid was dried at about 60° C. under vacuum for 4 h to provide nitisinone (136 g) as a white to yellowish solid, with a purity of 99.94% and a 99.8% assay measured by HPLC and a d(90) particle size between 310 and 350 µm. The content of potential genotoxic impurity no 4 resulted below 1 ppm.

Stability Studies

As evidenced in Table 1, nitisinone obtained through the process of the invention resulted extremely stable even in accelerated conditions for a period of at least six months. Importantly, the potentially genotoxic impurity-4 resulted below the limit of quantification, independently from the storage conditions. The presence of impurity-4 was checked by reverse HPLC/MS using the method described in the table underneath.

| Column | Ascentis Express C18 5 µm, 250 × 4.6 mm | | |
|---|---|---|---|
| Flow | 1 ml/minute | | |
| Injection volume | 10 µl | | |
| Wavelength | 235 nm | | |
| Column temperature | 30° C. | | |
| Detector MS | Polarity: positive; SIM Mode; m/z = 330 | | |
| | Gas temp: 300° C. | | |
| | Gas flow: 13.1 l/min | | |
| | Nebulizer: 20 psi | | |
| | Capillary: 4500 nA | | |
| | Step 0 to SIM > to MS | | |
| | Step 1 to SIM > to waste | | |
| Mobile phase A | CH₃CN | | |
| Mobile phase B | H₂O/0.1% TFA | | |
| HPLC Gradient | Time | % A | % B |
| | 0 | 50 | 50 |
| | 10 | 70 | 30 |
| | 12 | 70 | 30 |
| | 13 | 50 | 50 |
| | 23 | 50 | 50 |
| Retention time | 5.8 minutes | | |

TABLE 1

| Tests | Specifications | 6 months | 9 months | 6 months | 9 months | 6 months |
|---|---|---|---|---|---|---|
| Appearance (Visual) | While to yellowish crystalline powder | C | C | C | C | C |
| Water content (KF) | NMT 0.5% w/w | 0.0% | 0.0% | 0.2% | 0.0% | 0.2% |
| Assay-on anhydrous basis (HPLC) | 98.0-102.0% | 98.8% | 98.8% | 99.4% | 101.4% | 100.4% |
| Impurity-1 | NMT 0.15% | <0.01% | <0.01% | <0.01% | <0.01% | <0.01% |
| Impurity-2 | NMT 0.15% | <0.01% | <0.01% | <0.01% | <0.01% | <0.01% |
| Impurity-3 | NMT 0.15% | <0.01% | <0.01% | <0.01% | <0.01% | <0.01% |
| Impurity 4 | NMT 10 ppm | <5 ppm | <5 ppm | <5 ppm | <5 ppm | <5 ppm |
| Impurity 5 | NMT 0.15% | 0.01% | <0.01% | 0.01% | <0.01% | 0.01% |
| Any unspecified impurities | NMT 0.10% | <0.01% | <0.01% | <0.01% | <0.01% | <0.01% |
| Total impurities | NMT 0.50% | 0.01% | <0.01% | 0.01% | <0.01% | 0.01% |

C = Conform; NMT = No more than

The invention claimed is:

1. A process of synthesis of 2-(2-nitro-4-trifluoromethyl-benzoyl)-1,3-cyclohexanedione crystalline Form A, comprising:
   a) reacting 2-nitro-4-(trifluoromethyl) benzoyl chloride and 1,3-cyclohexanedione in a $CH_3CN$ solution in the presence of potassium carbonate;
   b) acidifying by means of HCl 37% to about pH=1 and warming to about 55° C.;
   c) washing the organic phase and concentrating it to about half the initial volume of $CH_3CN$ used in a);
   d) adding the crude nitisinone from c) to about an 3/1 (w/w) binary acetonitrile/toluene mixture, wherein the ratio nitisinone/binary mixture is around ¼ (w/v) and heating the resultant combination at a temperature of about 55° C. until complete dissolution;
   e) concentrating the solution from d) to a final volume of about twice the initial volume of toluene added in d) at a temperature below 50° C. to obtain a solution of nitisinone in toluene containing about 0.5-0.6 g of nitisinone per ml of solvent;
   f) adding toluene to the mixture obtained in e) in order to double the final volume obtained from e);
   g) repeating e);
   h) heating the product of g) to about 55° C. for about 1 hour;
   i) cooling the product resulting from h) to about 10° C. in about 10 to about 12 h;
   j) filtering off the solid thus obtained in i) and rinsing it with toluene pre-cooled to 0° C.; and
   k) drying the resulting crystals under vacuum at a temperature of about 60° C. for about 4 hours,
   wherein 2-(2-nitro-4-trifluoromethylbenzoyl)-1,3-cyclohexanedione crystalline Form A has a X-ray powder diffraction pattern with at least five specific peaks at about 2-theta=7.4, 14.7, 15.7, 22.9, and 29.7, wherein said values may be plus or minus 0.2° 2-theta and have an intensity of at least 30%.

2. The process according to claim 1, wherein the purity of 2-(2-nitro-4-trifluoromethylbenzoyl)-1,3-cyclohexanedione crystalline Form A obtained in j) is greater than 98%.

3. The process according to claim 1, wherein the amount of each single impurity is less than 0.05%.

4. 2-(2-Nitro-4-trifluoromethylbenzoyl)-1,3-cyclohexanedione crystalline Form A which has a X-ray powder diffraction pattern with at least five specific peaks at about 2-theta=7.4, 14.7, 15.7, 22.9, and 29.7, wherein said values may be plus or minus 0.2° 2-theta and have an intensity of at least 30%.

5. The crystalline 2-(2-nitro-4-trifluoromethylbenzoyl)-1,3-cyclohexanedione of claim 4, which has a X-ray powder diffraction pattern with at least ten specific peaks at about 2-theta=7.4, 14.7, 15.7, 22.9, 23.5, 23.8, 25.7, 29.7, 30.3, and 31.9, wherein said values may be plus or minus 0.2° 2-theta.

6. The crystalline 2-(2-nitro-4-trifluoromethylbenzoyl)-1,3-cyclohexanedione of claim 5, with a purity of at least 99.94%.

7. The crystalline 2-(2-nitro-4-trifluoromethylbenzoyl)-1,3-cyclohexanedione of claim 6, containing less than 10 ppm of 2-[3-nitro-4-(trifluoromethyl)benzoyl]-1,3-cyclohexanedione.

8. The crystalline 2-(2-nitro-4-trifluoromethylbenzoyl)-1,3-cyclohexanedione of claim 7, containing less than 5 ppm of 2-[3-nitro-4-(trifluoromethyl)benzoyl]-1,3-cyclohexanedione.

9. The crystalline 2-(2-nitro-4-trifluoromethylbenzoyl)-1,3-cyclohexanedione of claim 8, containing less than 1 ppm of 2-[3-nitro-4-(trifluoromethyl)benzoyl]-1,3-cyclohexanedione.

10. The crystalline 2-(2-nitro-4-trifluoromethylbenzoyl)-1,3-cyclohexanedione of claim 7, containing less than 0.05% of any single impurity after storage for six months at a temperature of 40° C. and 75% relative humidity, wherein said impurity is selected from the group consisting of 2-nitro-4-(trifluoromethyl) benzoic acid, 1,3-cyclohexanedione, 4-(trifluoromethyl)salicylic acid, and 6-trifluoromethyl-3,4-dihydro-2H-xanthene-1,9-dione.

11. 2-(2-Nitro-4-trifluoromethylbenzoyl)-1,3-cyclohexanedione crystalline Form A, obtainable by the process of claim 1.

12. A pharmaceutical composition comprising the crystalline 2-(2-nitro-4-trifluoromethylbenzoyl)-1,3-cyclohexanedione according to claim 4.

13. The pharmaceutical composition according to claim 12 comprising less than 1 ppm of 2-[3-nitro-4-(trifluoromethyl)benzoyl]-1,3-cyclohexanedione.

* * * * *